United States Patent
Allard et al.

(10) Patent No.: US 8,518,113 B2
(45) Date of Patent: Aug. 27, 2013

(54) INTERVERTEBRAL IMPLANT AND METHODS OF IMPLANTATION AND MANUFACTURE

(75) Inventors: Randall N. Allard, Germantown, TN (US); Jason J. Eckhardt, Memphis, TN (US); Tom J. Francis, Memphis, TN (US); William J. Albans, Memphis, TN (US); Thomas A. Carls, Memphis, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 970 days.

(21) Appl. No.: 12/123,623

(22) Filed: May 20, 2008

(65) Prior Publication Data

US 2009/0292362 A1    Nov. 26, 2009

(51) Int. Cl.
*A61F 2/44*    (2006.01)

(52) U.S. Cl.
USPC ..................................... 623/17.11

(58) Field of Classification Search
USPC .......... 623/17.11–17.16, 20.15, 21.16, 21.17; 606/246
See application file for complete search history.

(56) References Cited

U.S. PATENT DOCUMENTS

| | | | |
|---|---|---|---|
| 5,473,010 A | 12/1995 | Morita et al. | |
| 6,368,350 B1 * | 4/2002 | Erickson et al. | ........... 623/17.14 |
| 2005/0015151 A1 | 1/2005 | Fortin et al. | |
| 2005/0182494 A1 * | 8/2005 | Schmid | ......................... 623/23.5 |
| 2006/0224240 A1 | 10/2006 | Allard et al. | |
| 2007/0027546 A1 * | 2/2007 | Palm et al. | .................. 623/17.16 |
| 2007/0270958 A1 * | 11/2007 | Albans et al. | .............. 623/17.11 |
| 2008/0086127 A1 | 4/2008 | Patterson et al. | |
| 2008/0234687 A1 * | 9/2008 | Schaller et al. | .................. 606/90 |

FOREIGN PATENT DOCUMENTS

| | | |
|---|---|---|
| DE | 2804936 A1 | 8/1979 |
| WO | 03099172 A1 | 12/2003 |

OTHER PUBLICATIONS

Satellite Interdiscal Stabilization Sphere Surgical Technique, 2004, Medtronic Sofamor Danek, USA, Inc., 5 pages.
U.S. Appl. No. 12/038,992, filed Feb. 28, 2008.

* cited by examiner

*Primary Examiner* — Pedro Philogene
*Assistant Examiner* — David Comstock (57) ABSTRACT

In one aspect, an intervertebral prosthetic device for implantation within a disc space between adjacent first and second vertebral endplates includes a body including a main body with an outer surface bearing portion configured to interface with and articulate relative to one of the first and second vertebral endplates. It also comprises an orientation protrusion shaped in a manner to at least partially inhibit rotation of the body in the disc space. The body is sized in at least one direction to fit inside a boundary defined by a travel path of the first vertebra relative to the second vertebra, the travel path forming an arc about a center of rotation of the first vertebra, the travel path being spaced from the center of rotation a distance substantially equivalent to the distance from the center of rotation to the second vertebral endplate.

20 Claims, 9 Drawing Sheets

INTERVERTEBRAL IMPLANT AND METHODS OF IMPLANTATION AND MANUFACTURE

TECHNICAL FIELD

Embodiments of the present disclosure relate generally to intervertebral implants and methods of implantation and manufacture.

BACKGROUND

Within the spine, the intervertebral disc functions to stabilize and distribute forces between vertebral bodies. It comprises a nucleus pulposus which is surrounded and confined by the annulus fibrosis.

Intervertebral discs are prone to injury and degeneration. For example, herniated discs typically occur when normal wear or exceptional strain causes a disc to rupture. Degenerative disc disease typically results from the normal aging process, in which the tissue gradually loses its natural water and elasticity, causing the degenerated disc to shrink and possibly rupture. Intervertebral disc injuries and degeneration may be treated by fusion of adjacent vertebral bodies or by replacing the intervertebral disc with an implant, also known as a prosthesis.

Although existing devices and methods of implantation in spinal implant applications have been generally adequate for their intended purposes, they have not been entirely satisfactory in all respects. For example, some conventional intervertebral implants within a intervertebral disc space have broad footprint designs shaped somewhat like a pillow. Many implants are designed to match the endplates of the vertebral bodies. Because of this, when the spine flexes, the vertebral endplate edges may impinge on the edges of the implant.

It would be advantageous to provide implant durability, compatibility, and anatomical harmony. Similarly, it would be an improvement to simplify, improve and reduce the cost of implant manufacturing. The devices and methods in this disclosure overcome one or more of the shortcomings of the prior art.

SUMMARY

In one exemplary aspect, the present disclosure is directed to an intervertebral prosthetic device for implantation within a disc space between adjacent first and second vertebral endplates. The prosthetic device comprises a body including a main body with an outer surface bearing portion configured to interface with and articulate relative to one of the first and second vertebral endplates. It also comprises an orientation protrusion shaped in a manner to at least partially inhibit rotation of the body in the disc space. The body is sized in at least one direction to fit inside a boundary defined by a travel path of the first vertebra relative to the second vertebra, the travel path forming an arc about a center of rotation of the first vertebra, the travel path being spaced from the center of rotation a distance substantially equivalent to the distance from the center of rotation to the second vertebral endplate.

In another exemplary aspect, the present disclosure is directed to a method of selecting a sized implant. The method includes estimating the location of a center of rotation of a first vertebral body relative to a second vertebral body, estimating a radial travel path about the center of rotation traveled by the first vertebral body, and selecting a prosthesis for implantation from a plurality of prostheses. The selected prosthesis is sized to not cross the path of travel in the disc space.

In yet another exemplary aspect, the present disclosure is directed to an intervertebral prosthesis implantable within a disc space, disposed between upper and lower vertebral endplates. The prosthesis includes a main body formed of medical-grade polymeric material. The main body includes an outer surface comprising an upper bearing portion and a lower bearing portion. At least one of the upper and lower bearing portions is configured to articulate relative to one of the upper and lower vertebral endplates. The at least one of the upper and lower bearing portions including fluid-receiving pores and having a hardness that permits deformation of the main body to expel the fluid from the pores under a load applied by the respective upper or lower vertebral endplate.

In yet another exemplary aspect, the present disclosure is directed to a method of forming and using an intervertebral prosthesis for implantation between adjacent vertebral bodies within an intervertebral disc space. The method includes the steps of providing a medical-grade polymer and providing a mold for creating the intervertebral prosthesis. The mold includes a main cavity shaped to form the prosthesis. The method also includes the steps of heating the polymer to a temperature between 600° and 800° Fahrenheit and injecting the polymer into the main cavity of the mold at a temperature between 300° and 500° Fahrenheit and at a pack pressure between 5,000 and 15,000 PSI until the main cavity is completely filled with the polymer with a peak pressure between 15,000 and 25,000 PSI. The method also includes the steps of holding the injected polymer in the mold at a hold pressure between 15,000 and 25,000 PSI, removing the polymer from the mold, and implanting the molded polymer between adjacent vertebral bodies within the intervertebral disc space of a patient.

DETAILED DESCRIPTION

For the purpose of promoting an understanding of the principles of the invention, reference is made to the embodiments, or examples, illustrated in the drawings, and specific language is used to describe the embodiments. It is nevertheless understood that no limitation of the scope of the invention is intended. Any alterations and further modifications of the described embodiments, and any further applications of the principles of the invention as described herein, are contemplated, as would normally occur to one skilled in the art to which the invention relates.

Figure 1A:
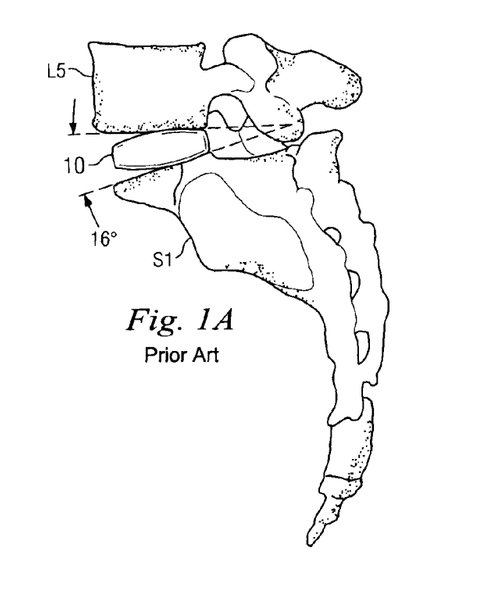
FIGS. 1A and 1B are illustrations of a conventional implant between L5 and S1 vertebral bodies in extension and in flexion.
Figure 1B:
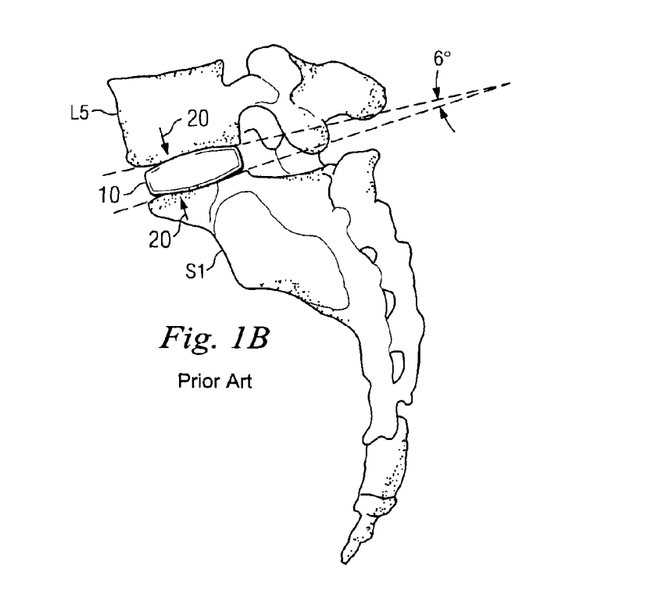

Referring now to FIGS. 1A and 1B, a conventional implant 10 is shown between two adjacent vertebral bodies, in this case, the L5 and S1 vertebrae. FIG. 1A shows the vertebrae in extension and FIG. 1B shows the vertebrae in flexion. As can be seen, the conventional implant 10 extends across the vertebral endplates. However, as the spine flexes, it pitches, causing impingement of the upper and lower vertebral bodies on the implant 10 during one or both of flexion and extension. In these embodiments, impingement is shown best in FIG. 1B, where the upper and lower vertebral endplates rotate together and pinch a section of the conventional implant 10. This impingement is identified by the arrows labeled with the reference numeral 20.

Impinging on the implant 10 limits the range of motion that can be traveled by the vertebral bodies. For example, FIGS. 1A and 1B also show the available range of motion at the joint shown. In FIG. 1A at maximum extension, the vertebral bodies form an angle of 16 degrees. In FIG. 1B, at maximum flexion, as limited by the pinching of the implant 10, the vertebral bodies form an angle of 6 degrees. Accordingly, the joint shown has an articulation range of 10 degrees.

An articulation range of 10 degrees, however, is less than that of a healthy vertebral joint. When prosthetic devices replace natural body parts, it often is the goal that the device mimic the natural abilities and properties of a healthy natural body part. A healthy natural vertebral joint may have an articulation range up to and beyond 21 degrees from a point of maximum flexion, such as when bending over to touch a floor, to a point of maximum extension.

Accordingly, what is needed is a device sized so that when flexion occurs the articulation occurs around the device and the incidence angle of the vertebral endplate does not impinge on the outer border of the device.

Figure 2:
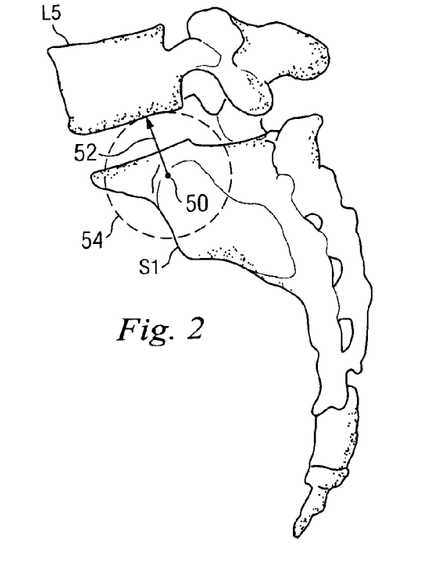
FIG. 2 is an illustration of a radial pathway of travel about a center of rotation of the L5 vertebral body relative to the S1 vertebral body.

FIG. 2 shows a kinematic center of rotation (COR) for the L5 vertebral body around the S1 vertebral body. The COR is identified by the center dot, reference by the numeral 50. From the COR, the distance to the vertebral endplate of the L5 vertebral body represents a radius of curvature 52. Accordingly, when the L5 vertebral body articulates relative to the S1 vertebral body, it travels along an arcing pathway 54 defined by a part of the radius of curvature 52. Accordingly, the pathway 54 defines an envelope or boundary that if exceeded by an implant, would limit the range of motion of the vertebral bodies.

Figure 3:
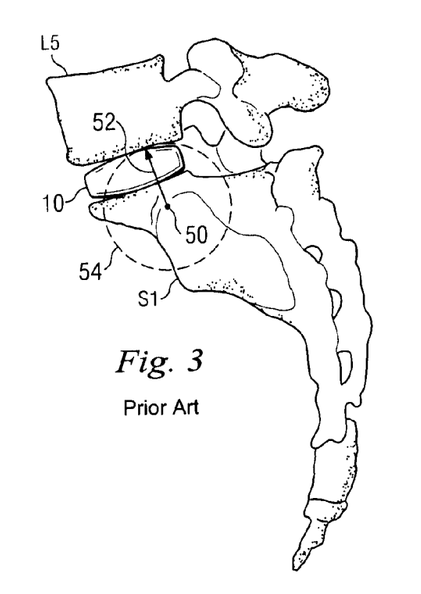
FIG. 3 is an illustration of a conventional implant between the L5 and S1 vertebral bodies relative to the pathway of travel of the L5 vertebral body relative to the S1 vertebral body.

FIG. 3 shows the L5 and S1 vertebral bodies of FIG. 2 with the conventional implant 10 therebetween, along with the pathway 54 defined about the COR. As shown, the conventional implant 10 extends along the vertebral endplates and protrudes through the boundary and into the pathway 52. For the conventional implant 10 to not be pinched during flexion, it would need to reside entirely within the pathway 54, or in other words, entirely within the boundary defined by the pathway 54.

Figure 4:
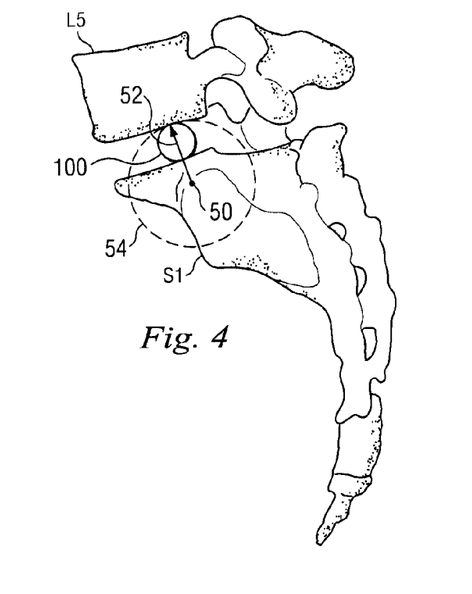
FIG. 4 is an illustration of an exemplary implantable prosthesis in accordance with the principles of this disclosure disposed between the L5 and S1 vertebral bodies relative to the pathway of travel of the L5 vertebral body relative to the S1 vertebral body.

FIG. 4 shows the L5 and S1 vertebral bodies of FIG. 2 with an implantable prosthesis, referenced herein by the numeral 100 disposed therebetween. The COR and pathway 54, as described above, are shown in FIG. 4. As can be seen, the implantable prosthesis 100 is entirely contained within the boundary defined by the pathway 54. In other words, the prosthesis is oriented so that the prosthesis is entirely within the pathway 54 defined by a path of travel about a COR for the adjacent vertebrae.

Figure 5A:
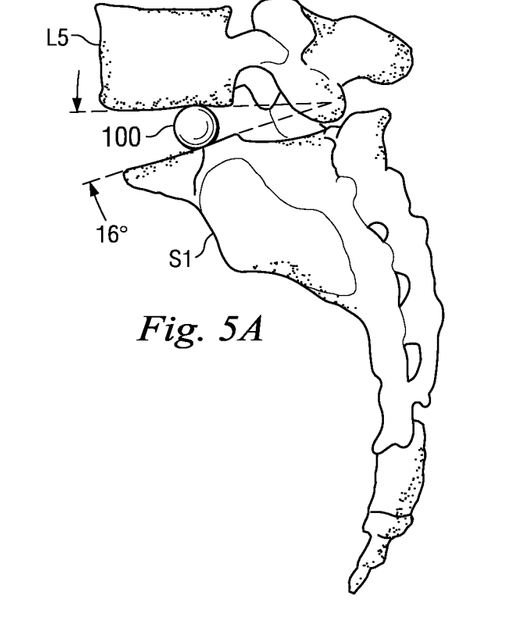
FIGS. 5A and 5B are illustrations showing the prosthesis of FIG. 4 in accordance with the principles of this disclosure between L5 and S1 vertebral bodies in extension and in flexion.
Figure 5B:
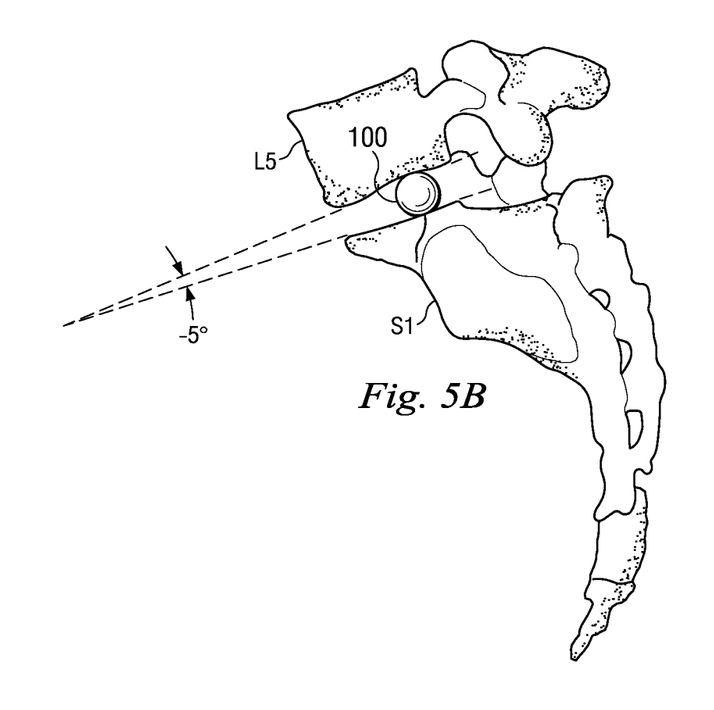

FIGS. 5A and 5B show the range of articulation of the vertebral bodies L5 and S1 with the implantable prosthesis 100 disposed therebetween. FIG. 5A shows the joint in extension and FIG. 5B shows the joint in flexion. In extension, the vertebral endplates form an angle of 16 degrees, without impingement of the vertebral endplates on the implant 100. In flexion, the vertebral endplates form an angle of −5 degrees without impingement on the implant 100. Thus, the range of articulation for the joint is 21 degrees.

The increase in the range of articulation when compared to the conventional device in FIGS. 1A and 1B is a result of the lack of impingement by the endplates on the prosthesis. In turn, this is because the prosthesis 100 is sized and shaped to have a width (in at least one direction) less than the distance of the disc space encompassed by the pathway or boundary 54.

Figure 6:
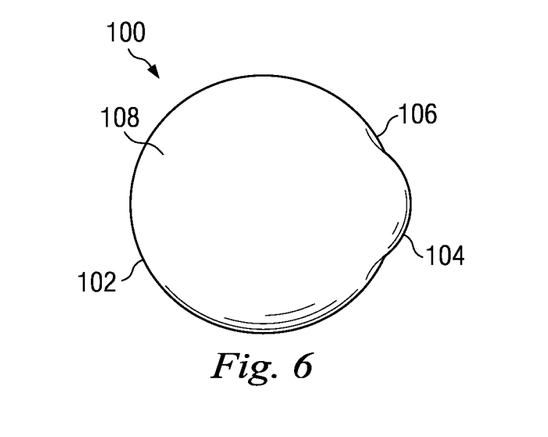
FIG. 6 is an illustration of a perspective view of an exemplary implantable prosthesis in accordance with the principles of the present invention.

FIG. 6 shows an exemplary embodiment of the prosthesis 100. The intervertebral replacement prosthesis 100 has a generally spherical main body 102. A semi-spherical orientation protrusion 104 extends from a side of the main body 102. A transitional segment 106 connects the exterior surfaces 108 of the main body 102 and the orientation protrusion 104. The surface 108 of the main body 102, orientation protrusion 104, and transitional segment 106 may have various degrees of roughness. The prosthesis 100 may be configured for placement in a disc space between vertebral endplates of adjacent vertebrae. Accordingly, the surface 108 may include upper and lower bearing surfaces configured to interface with and articulate relative to the endplates.

The roughness may be generally distributed across the surface 108 or may be arranged on the surface 108 in configurations that may be referred to as areas, patterns, designs or other similar terms. It is envisioned that the prosthesis 100 may have varied types of surface 108. The surface 108 may vary, which may be measured in distance from the apex of a raised peak to the base of an indentation of roughness. In some embodiments, the prosthesis 100 may have a relatively smooth area of surface 108 varying by less than 2 microns. In other embodiments, the prosthesis 100 may have of a relatively smooth area of surface 108 varying by less than 1 micron, and in yet other embodiments, by less than 0.5 microns, less than 0.25 microns, or by less than 0.1 microns. Similarly, it is also envisioned that the prosthesis 100 may have a relatively rough area of surface 108 varying by more than 0.5 microns, by more than 1 micron, or by more than 2 microns, for example. In some embodiments, a single prosthesis 100 may have a surface 108 with areas of either or both relative roughness and relative smoothness.

The interior of the prosthesis 100 may be of a single substance or compound, or may be a composite of materials. The prosthesis 100 may be formed from an appropriate medical-grade polymer including, but not limited to, polyetherketones (PEK), members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); cross-linked UHMWPE; polyurethane (PU) and nano-material reinforced polymers. Polymers, including PEEK, provide, among other things, a benefit of being MRI compatible.

When formed of a radiolucent material, such as PEEK, the prosthesis 100 is virtually invisible to detection by x-ray. This enhances the visualization of surrounding tissue without blocking the radiographic view. Radiopaque markers or materials, for example, barium sulfate, $BaSO_4$, may be added to the prosthesis 100 to enhance visualization. Still further, varied areas of the prosthesis 100 in alternative embodiments include differing or distinguishable radiopaque elements or markers to assist in visualization during or after implantation. In one form, the main body 102, one segment of the prosthesis, includes a first radiopaque marker, and the orientation protrusion 104, an additional segment of the prosthesis, includes a second radiopaque marker. The first marker is remotely distinguishable from the second marker, such as providing distinct imaging characteristics in an x-ray image. Alternatively, shaped radiopaque elements may be oriented within the main body 102, such that the orientation of the radiolucent prosthesis 100 is determinable by the orientation of the shaped radiopaque element. For example, the radiopaque element may be oriented relative to the orientation protrusion so that the location of the orientation protrusion may be tracked relative to the location of the main body 102. In some examples, the radiopaque marker is cylindrically shaped and extends within the prosthesis 100 from the orientation protrusion.

Figure 7:
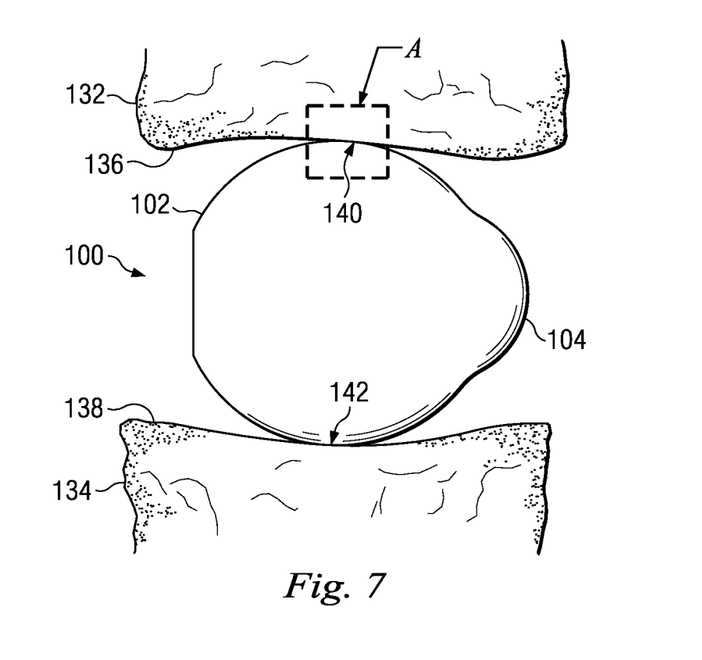
FIG. 7 is an enlarged scale, vertically foreshortened, somewhat schematic, lateral view of an exemplary intervertebral replacement prosthesis implanted in an unloaded vertebral column section.

Referring to FIG. 7, an exemplary prosthesis 100 (not shown to scale) is shown inserted between an upper vertebra 132 and a lower vertebra 134. The upper vertebra 132 and the lower vertebra 134 have an upper endplate 136 and a lower endplate 138, respectively. Upper and lower endplates 136, 138 contact the main body 102 of prosthesis 100 at upper bearing implant interface 140 and lower bearing implant interface 142, respectively.

Orientation protrusion 104 may rotate to contact either the upper vertebra 132 or the lower vertebra 134, but the combined geometry of the main body 102 and the orientation protrusion 104 are intended to keep the orientation protrusion 104 in a position intermediate upper vertebra 132 and lower vertebra 134, thereby at least partially inhibiting rotation of the prosthesis in the disc space.

Figure 8:
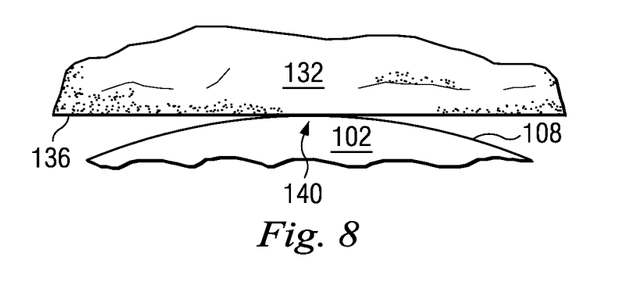
FIGS. 8 and 9 collectively illustrate, at a greatly enlarged scale, a cross-sectional side view of the application of a load to the implant interface of the detail area A, of FIG. 7.
Figure 9:
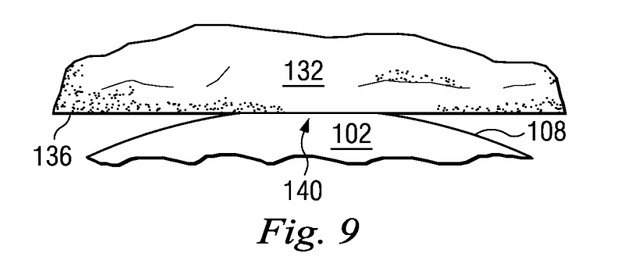

FIGS. 8 and 9 show details of an area A of FIG. 7 that encompasses a part of the upper implant interface 140. Referring now to FIGS. 8 and 9, a depiction is provided of an exemplary desirable response of the surface 108 as it comes in contact with the endplate 136. Unlike hard metals, such as titanium, that are currently used in making vertebral prostheses, which tend to cause the endplate 106 to subside around the harder metal prosthesis, the polymeric prosthesis 100 may have a modulus that more closely replicates bone and may be constructed to yield at the implant interface 140. As such, the implant interface 140 expands from a single point in contact with the endplate 106 (as shown in FIG. 8) to a larger area (as shown in FIG. 9), thereby distributing the force of the load. In this way, load on the vertebral column causes less force on individual points on endplate 106.

In some embodiments, the polymeric prosthesis 100 may be formed of a polymeric material having a hardness within the range of 70-100 Durometer Shore D. In other embodiments, the polymeric material may have a hardness within the range of 80-90 Durometer Shore D. Within these ranges, the polymeric prosthesis 100 has a hardness that more closely mimics the properties of bone than traditional metal implants. As such, prostheses formed of these materials provide better flexibility, dampening, and are more resistant to subsidence than metal-formed prostheses. In addition, such implants may allow remodeling of the bone to occur around the prosthesis. This may help redistribute loads of the spinal segment away from other structures, such as the annulus or facets, to share the load.

Figure 10:
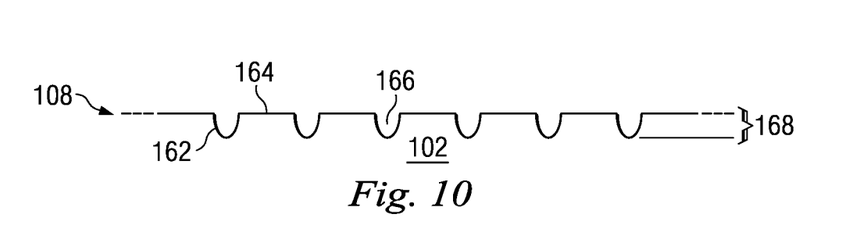
FIG. 10 is an extremely enlarged scale schematic depiction of a cross-sectional side view of a pocketed surface of an exemplary prosthesis of the present disclosure.

Referring now to FIG. 10, the surface 108 of the main body 102 is shown to have a uniform roughness to a degree that pockets 162 are formed in the surface 108. Intermediate the pockets 162 are crowns 164 that are raised relative to the interior wells 166 of the pockets 162. The pocket depths 168 are the distance the crowns are removed from the bottom of the wells 166. The pocket depths 168 may be considered variations in the surface 108.

Figure 11:
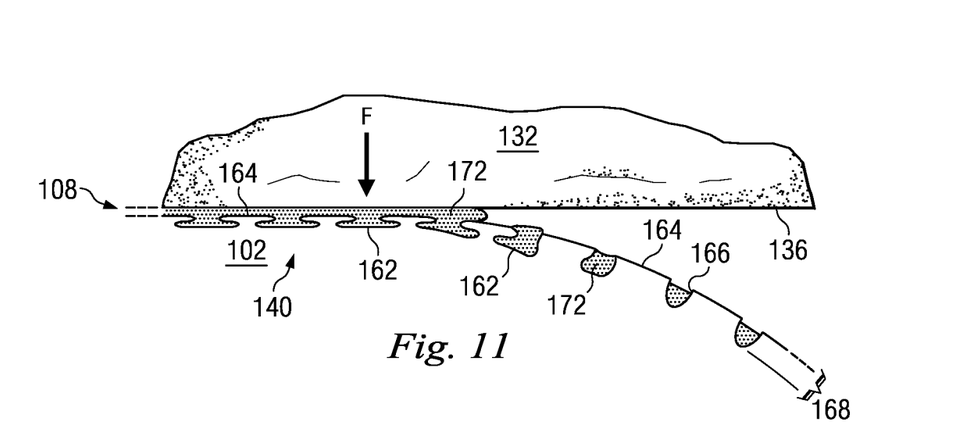
FIG. 11 is an extremely enlarged scale somewhat schematic depiction of a cross-sectional side view of a loaded implant interface, as in detail area A, with a pocketed surface of an exemplary prosthesis of the present disclosure.

Referring to FIG. 11, the surface 108 of an exemplary main body 102 has pockets 162 and crowns 164. In the exemplary embodiment, surface 108 is formed from an elastically deformable material, such that pockets 162 and crowns 164 are deformable under contact load applied so as to force the main body 102 against endplate 136 of the upper vertebra 132. The exemplary load force F is great enough to deform the material of main body 102, compressing the pocket 162 toward the crown 164. In other words, the load force F reduces the pocket depth 168.

In the exemplary embodiment, a coating material fluid 172 is provided that occupies the wells 166. As a pocket 162 is compressed fluid 172 is expelled from the well 166, and is spread across the adjacent crown 164, and generally over the surface 108. The fluid 172 may be drawn back into the well 166 as the load force F is reduced so that the material of main body 102 is permitted to elastically recover. Fluid 172 may be a wetting material or a lubricant, such as hyaluronic acid (HA). Additionally, fluid 172 may be a bone morphogenetic protein. In some embodiments, the fluid 172 is imbibed bodily fluid from the patient's body. The fluid 172 may decrease the friction against the bone and may enhance insertion info the disc space. Further, it may decrease wear against the cartilaginous endplates. Furthermore, improved lubricity may enhance the life of the device, improve possible pain response against cartilage, and may reduce wear that may contribute to subsidence. Furthermore, the coating may allow the device to self-center within the natural sulcus of the vertebral endplate, allowing a better fit.

It is envisioned that in some embodiments, the pocket depth 168 may be less than 5 microns. In other embodiments, the pocket depth 168 may be less than 2 microns, may be less than 1 micron, may be less than 0.5 microns, may be less than 0.25 microns, or may be less than 0.1 microns, for example.

In some embodiments, the pockets 162 may be formed within the outer surface 108 of the main body 102 by a laser etching process that creates the indentations for reception of fluids. Laser etching provides control and tight regulation of the characteristics of the pockets. The pockets 162 also may be formed by a roughening process configured to introduce imperfections into the outer surface 108 that are sufficient to retain fluid. Other processes also may be suitable. In some embodiments, outer surface 108 is formed of a material having sufficient porosity to receive and expel the fluid in the manner described above.

Figure 12:
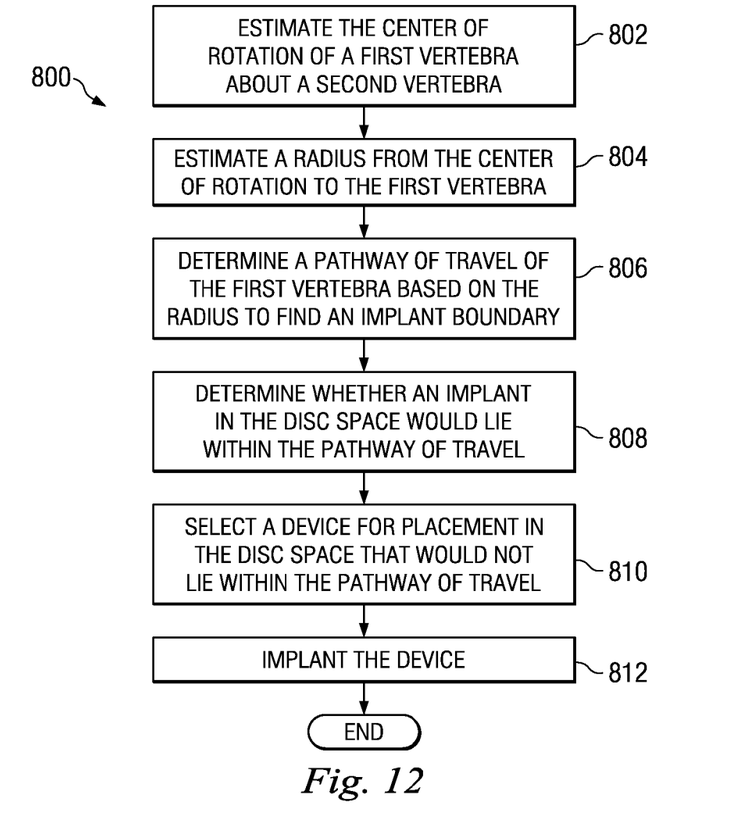
FIG. 12 is a flow-chart of a method of selecting a sized prostheses for implantation in a patient.

FIG. 12 is a flow-chart 800 detailing a method of selecting a sized implant for implantation into a patient. At a step 802, a health provider estimates the center of rotation of a first vertebra, such as the L5 vertebra, about a second vertebra, such as the S1 vertebra. This may be done using any of a number of different approaches. In one example, the COR is determined using a series of X-ray images taken with the vertebrae at different locations within the range of motion. Comparing the location of the first vertebra relative to the second vertebra at more than one position in the flexion/extension range may allow a provider to estimate the COR. In another example, the COR may be determined using a continuous fluoroscopy process where the patient moves through a range of motion. Again, comparison of the first vertebra relative to the second vertebra at a series of locations can be used to identify the COR. Other methods also may be used.

At a step 804, the provider estimates a radius from the center of rotation to the first vertebra. This may be easily determined by viewing the X-ray or fluoroscopy images. It should be noted that estimating the radius need not include determining the length in units, such as centimeters or inches, but may include merely noting, such as for example with a compass, the distance from the center of rotation to the endplate of the first vertebra.

At a step 806, the provider determines a pathway of travel of the first vertebra based on the estimated radius. For example, as it articulates about the COR, the first vertebra may follow an arcing path matching the radius. This pathway may serve as a reference boundary or envelope defined by the pathway.

At a step 808, the provider determines whether an implant in the disc space would extend into the pathway of travel. In some embodiments, the provider may determine whether an implant would extend into the path of travel by measuring a distance along the vertebral endplates from the path of travel at one side of the disc space to the path of travel at the other side of the vertebral disc space. This represents the maximum width that an implant may have without being pinched by the vertebral endplates during flexion or extension. An implant with a greater width would extend through the pathway of travel, and an implant with a smaller width would not extend through the pathway of travel, so long as it is properly placed.

At a step 810, the provider selects a prosthesis having a width that would not extend through the pathway of travel. If the prosthesis has a larger width in one direction and a smaller width in the other direction, the provider may consider the direction the prosthesis will sit within the disc space when making this determination. At a step 812, the prosthesis is implanted within the disc space using conventional procedures.

The prosthesis may be subjected various types of processing during processing or implantation. For example, the prosthesis may be coated with one or more materials in order to obtain specific desired exterior surface characteristics. Suitable coating materials may include polycarbonates, polyethers, silicone enhanced, silicone modified, and silicone dipped polyurethanes, lubricants, and wetting agents. In other embodiments, ceramic materials such as aluminum oxide or alumina, zirconium oxide or zirconia, compact of particulate diamond, or pyrolytic carbon are suitable coating materials. In some embodiments, the main body may be coated with an integral outer layer having improved wear resistance. For example, the outer coating may be formed of a PU having harder properties than the remaining portions of the prosthesis.

In some embodiments, the prosthesis is molded to include openings suitable for receiving installation tools. In other embodiments, the openings are prepared by any of various methods including drilling, machining, or other suitable methods. Once the openings are prepared tools may be inserted into the openings to test the fit.

In some embodiments markers are added to the prosthesis to provide radiological detection. Various suitable markers can be embedded or blended into the polymer compound so that the prosthesis becomes radiopaque. Additionally, visual markers can be added by vapor-honing, laser etching, or other appropriate methods.

Figure 13:
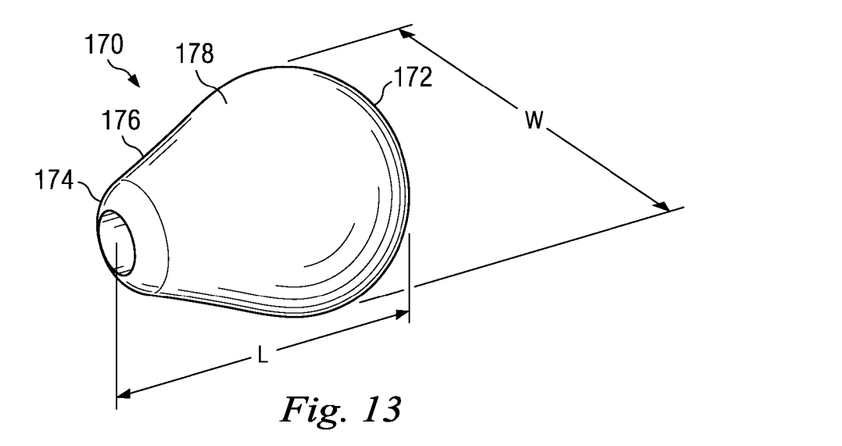
FIG. 13 is a perspective view of an alternate exemplary intervertebral replacement prosthesis of the present disclosure.

Referring now to FIG. 13, an alternate exemplary prosthesis 170 suitable for fitting within the travel path is described herein. The prosthesis includes a generally spherical main body 172 that forms the bearing portions, with an orientation protrusion 174 extending away from a side of the main body 172. Transitional segment 176 extends tangentially from the surface 178 of main body 172 to intersect tangentially with the surface of the orientation protrusion 174. In alternate exemplary embodiments, transitional segment 176 may curve convexly or concavely from the main body 172 to the orientation protrusion 174, depending on the desired geometry of the prosthesis 170. Other modifications to the surface 178 of the prosthesis 170 may include flat segments, grooved segments, and generally non-spherical segments.

Here, because the prosthesis 170 may rotate after implantation so that the orientation protrusion 174 may by posterior, anterior, or lateral, within the disc space, for purposes of determining whether the prosthesis would fit within the boundary identified by the travel pathway of one vertebra relative to the other, it is contemplated that the minimum of the length and width (marked L and W respectively in FIG. 13) would be considered. For example, during flexion and extension, impingement of the upper and lower vertebrae on the orientation protrusion 174 may cause the prosthesis 170 to spin with the disc space so that the orientation protrusion 174 is laterally disposed within the disc space. Thus, it avoids limiting the range of movement of the spine in flexion and extension. The width W of the prosthesis 170 may be considered then for purposes of determining whether the prosthesis will extend into the travel pathway of the vertebral bodies. Naturally, if the implanted prosthesis were configured to be fixed in place in the disc space, its fixed position relative to the travel pathway of the vertebral bodies would be considered.

Figure 14:
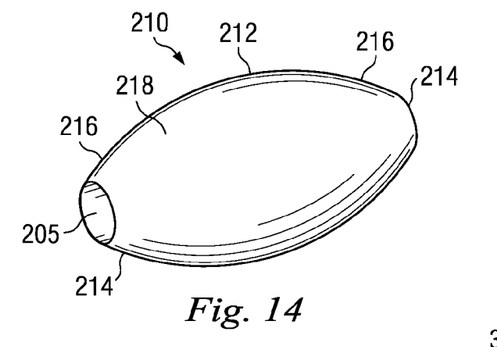
FIG. 14 is a perspective view of an additional alternate exemplary prosthesis of the present disclosure.

Referring now to FIG. 14, an additional alternate exemplary prosthesis 210 has the general shape of an elongated, narrow prolate spheroid. Here, the main body 212 is positioned intermediate to a pair of orientation protrusions 214 joined to form an integral surface 218 by a pair of transitional segments 216. In alternate exemplary embodiments, transitional segments 216 may curve either or both convexly or concavely from the main body 212 to the orientation protrusion 214, depending on the desired geometry of the prosthesis 210. Connection 205, configured to connect to an installation tool, is positioned in one orientation protrusion 214. As described above, because during flexion and extension, the prosthesis may align itself so that its orientation protrusions are laterally disposed. For purposes of determining whether the prosthesis would fit within the boundary identified by the travel pathway of one vertebra relative to the other, it is contemplated that the minimum of the length or the width (marked L and W respectively in FIG. 13) would be considered.

Figure 15:
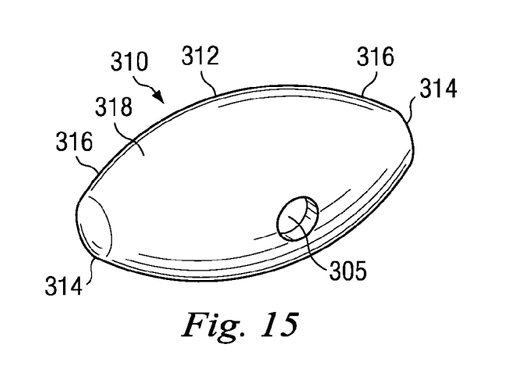
FIG. 15 is a perspective view of an additional alternate exemplary prosthesis of the present disclosure.

Referring now to FIG. 15, an additional alternate exemplary prosthesis 310 has the general shape of an elongated, narrow prolate spheroid. The main body 312 is positioned intermediate to a pair of orientation protrusions 314 joined to form an integral surface 318 by a pair of transitional segments 316. In alternate exemplary embodiments, transitional segments 316 may curve either or both convexly or concavely from the main body 312 to the orientation protrusion 314, depending on the desired geometry of the prosthesis 310. Connection 305, configured to connect to an installation tool, is positioned in main body 312. Again, for purposes of determining whether the prosthesis would fit within the boundary identified by the travel pathway of one vertebra relative to the other, it is contemplated that the minimum of the length and width would be considered.

Figure 16:
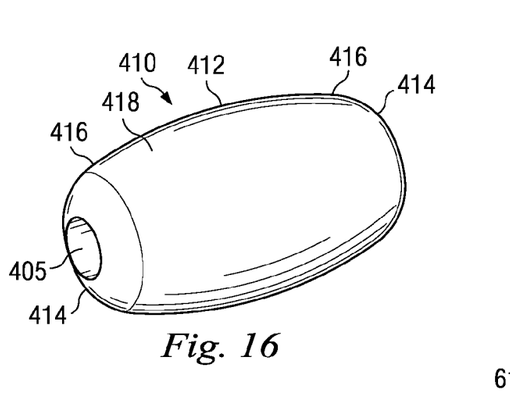
FIG. 16 is a perspective view of an additional alternate exemplary prosthesis of the present disclosure.

Referring now to FIG. 16, an additional alternate exemplary prosthesis 410 has the general shape of an elongated, slowly tapered prolate spheroid. The main body 412 is positioned intermediate to a pair of orientation protrusions 414 joined to form an integral surface 418 by a pair of transitional segments 416. In alternate exemplary embodiments, transitional segments 416 may curve either or both convexly or concavely from the main body 412 to the orientation protrusion 414, depending on the desired geometry of the prosthesis 410. Connection 405, configured to connect to an installation tool, is positioned in one orientation protrusion 414.

Figure 17:
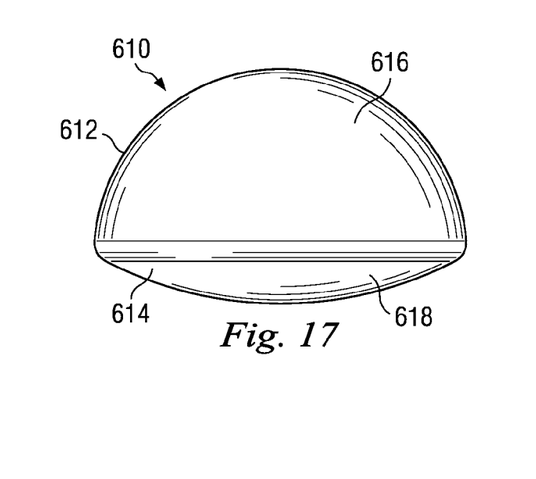
FIG. 17 is a perspective view of an additional alternate exemplary prosthesis of the present disclosure.

Referring to FIG. 17, prosthesis 610 has a main body 612 with a generally hemispherical shape. An orientation protrusion 614 extends from the truncated side of main body 612. The main body 612 has a significantly more acutely curved surface 616 than the surface 618 of the orientation protrusion 614, so the prosthesis 610 appears relatively flat on the side having the orientation protrusion 614.

Figure 18:
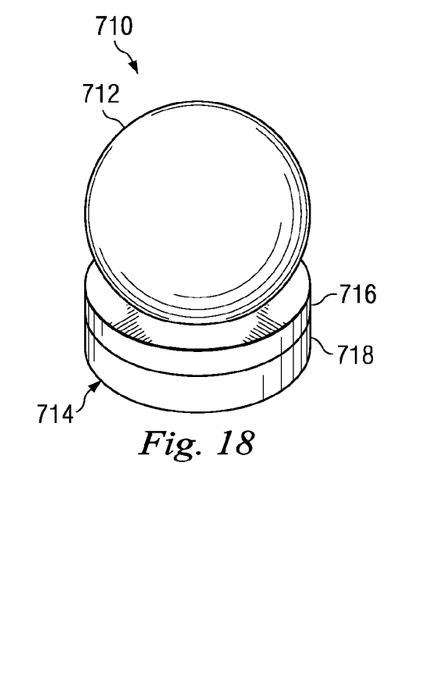
FIG. 18 is a perspective view of an additional alternate exemplary prosthesis of the present disclosure.
Figure 19:
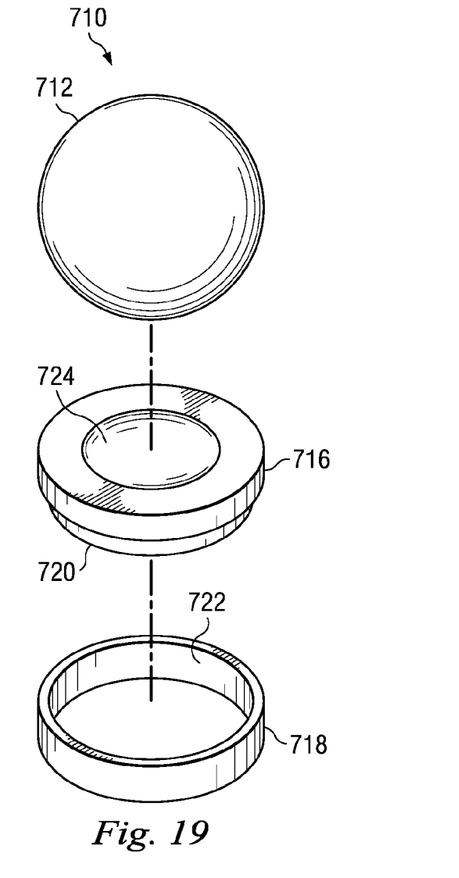
FIG. 19 is an illustration of a perspective view of the exemplary prosthesis of FIG. 20 in an exploded configuration.

Referring to FIGS. 18 and 19, a prosthesis 710 includes a spherical main body 712 and a prosthesis endplate 714. The main body 712 may be formed of any of the materials described herein. The endplate 714 may include an upper portion 716 and a lower portion 718. The upper portion 716 may be configured to interface with the main body 712 and the lower portion 718 may be configured to interface with the upper portion 716 and a vertebral endplate. In the embodiment shown, the upper endplate 716 has a protruding portion 720 configured to fit within a recess 722 formed in the lower endplate 718. In some embodiments, the recess 722 may have a groove around its edge configured to fit a corresponding rim about the exterior of the protruding portion 720. Thus, in some embodiments, the groove and rim may cooperate to snap the upper and lower endplates 716, 718 together and to secure them together. As best seen in FIG. 19, the upper endplate 716 includes a depression 724 that receives a bearing portion of the main body 712. In some embodiments, the depression 724 may be a bore that allows the main body 712 to sit more deeply than shown in FIG. 18, lowering the overall height of the prosthesis 710. In some embodiments, the upper and lower plates 716, 718 are formed of the same materials, while in other embodiments, they are formed of different materials. For example, the lower plate may be formed of a metal, such as Ti, while the upper plate is formed of a polymeric material, such as PEEK or PU. Other configurations also are contemplated. For purposes of determining whether the prosthesis would fit within the boundary identified by the travel pathway of one vertebra relative to the other, the entire prosthesis would be considered.

Figure 20:
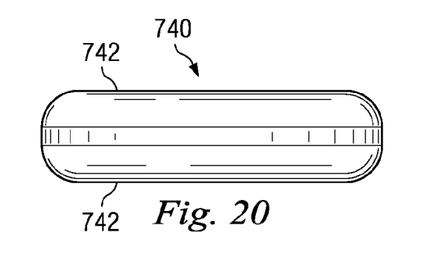
FIG. 20 is a side view of an additional alternate exemplary prosthesis of the present disclosure.
Figure 21:
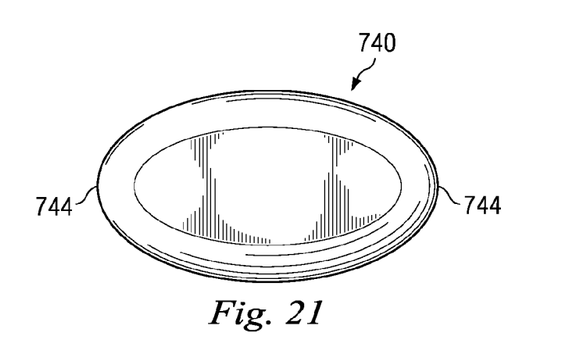
FIG. 21 is a top view of the exemplary prosthesis of FIG. 20.

Referring to FIGS. 20 and 21, a prosthesis 740 may have non-spherical geometries. The side view of the prosthesis 740, in FIG. 20, shows that the exemplary prosthesis 740 has two flat surfaces 742 and two extended sides 744. The flat surfaces 742 may be suitable for interfacing with the endplates of two adjacent vertebrae, as in FIGS. 4 and 7 above. So positioned, the two extended sides 742 extend over the general oval shape of a vertebra endplate to more thoroughly distribute a load applied to the spinal column.

While the disclosed implants may be made of any biocompatible material, in some embodiments, the implants are made from a polymeric material. Characteristics of implantable-grade or medical-grade polymers—such as biocompatibility, strength, flexibility, wear resistance and radiolucence—make them especially suitable for use in medical device applications such as intervertebral implants and disc nucleus augmentations or replacements.

The polymeric prostheses disclosed above, and other prostheses, may be manufactured out of polyetheretherketone (PEEK) using the following devices and methods. For the sake of clarity and without limitation, specific references will be made to manufacturing the various features of the prosthesis 100 disclosed above. It should be recognized that similar techniques and methods may be used for forming other prostheses, including the other prostheses disclosed herein, according to the present disclosure.

It is contemplated that the prostheses disclosed herein be used in expansion devices also. For example, in some embodiments, once implanted, a prosthesis may be deformable to a shape that better fits the natural sulcus of the endplates than the insertion shape. The deformation may be accomplished using mechanically expanding arrangements contemplated in the art.

Figures 22, 23:
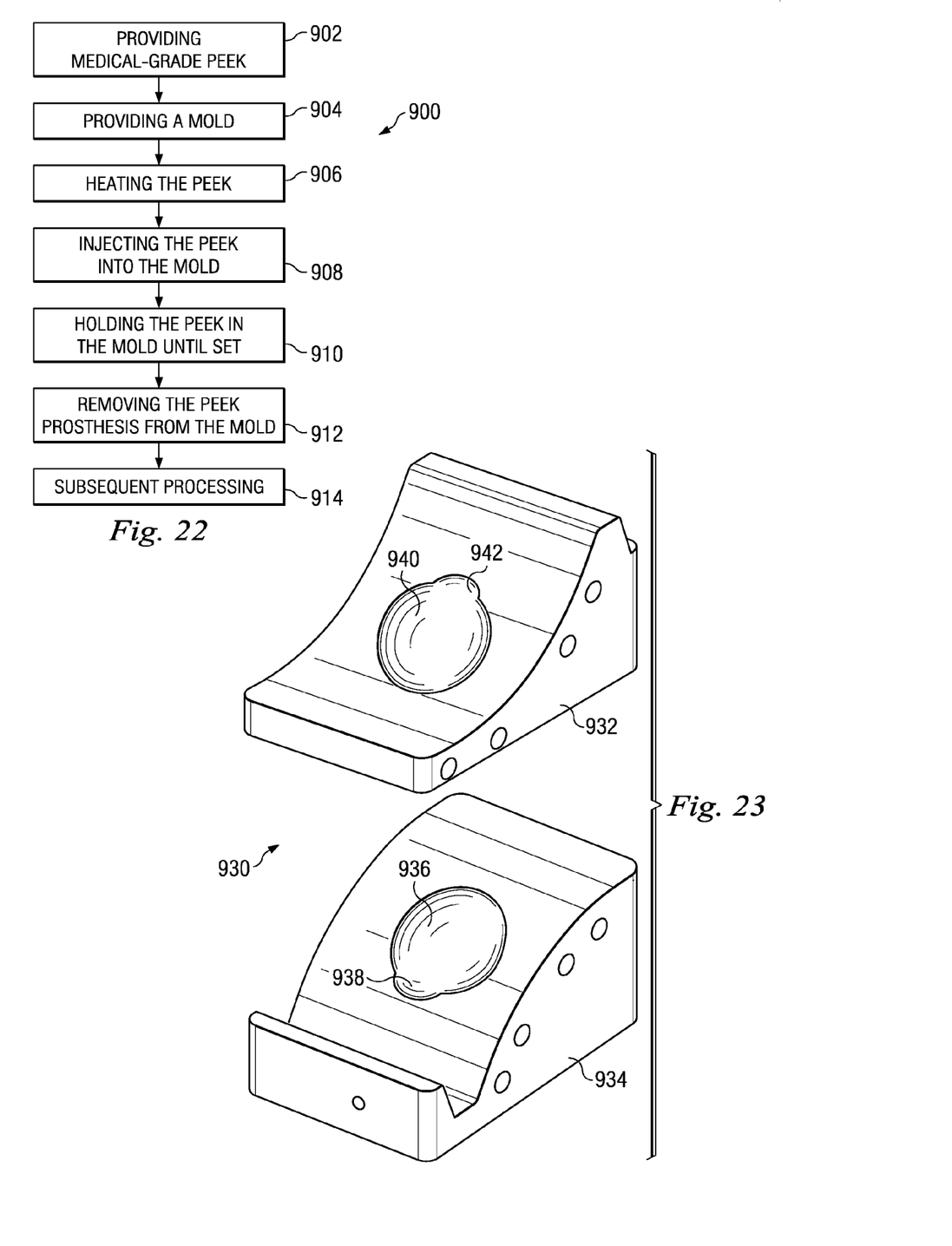
FIG. 22 is a flow-chart that embodies aspects of the present disclosure.
FIG. 23 is a diagrammatic perspective view of a prosthesis mold for an exemplary prosthesis of the present disclosure.

FIG. 22 is a flow-chart 900 illustrating an exemplary method of manufacturing prostheses that embody aspects of the present disclosure. The method includes the steps of providing medical-grade polyetheretherketone (PEEK) 902, providing a mold shaped for creating a prosthesis 904, and heating the PEEK 906. The method also includes the steps of injecting the PEEK into the mold 908, holding the injected PEEK in the mold until it sets 910; removing the PEEK prosthesis from the mold 912; and subsequent processing 914. The method can also include preparing and drying the PEEK.

With respect to providing the PEEK 902, medical-grade PEEK is used to form the prostheses. Medical-grade PEEK is available in various compounds, viscosities, and with various additives. For example, PEEK is available with additives such as carbon fiber and barium sulfate. The additives are used to change the physical properties of the PEEK, such as tensile strength and radiopacity. Similarly, PEEK is available in regular viscosity, high viscosity, and low viscosity. The use of high viscosity PEEK is advantageous for the prosthesis, which is likely to bear heavy loads. The use of low viscosity PEEK is advantageous where the prosthesis is to contain flexibility, create a thin cross-sectional layer, and other applicable situations. Medical-grade PEEK is commercially available from Invibio Biomaterial Solutions of Lancashire, UK under the trade-name PEEK-OPTIMA™. Normal viscosity PEEK-OPTIMA™ is available as product number LT1; lower viscosity PEEK-OPTIMA™ is available as product number LT2; and even lower viscosity PEEK-OPTIMA™ is available as product number LT3. The actual properties of the PEEK material chosen can affect the desired temperature and pressure parameters for the method. For illustration purposes and without limitation, the method described herein may utilize regular viscosity PEEK-OPTIMA™ (LT1).

In other embodiments, polymers other than the various PEEK compounds may be used. For example, suitable polymers include polyetherketone (PEK); members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); cross-linked UHMWPE; and nano-material reinforced polymers. The actual properties of the polymer material chosen can affect the desired temperature and pressure parameters for the method.

With respect to providing the mold 904, FIG. 23 is a diagrammatic perspective view of a prosthesis mold 930 that embodies aspects of the present disclosure. The mold 930 is adapted for use in the injection molding and compression molding of PEEK into intervertebral prostheses. As such, the mold 930 is configured for use with and in other machinery and is able to withstand the high temperatures and high pressures of the manufacturing process. The mold 930 includes a lower piece 932 and an upper piece 934. In use, the upper piece 934 is securely fitted to the lower piece 932. The seal between the upper and lower pieces 934 and 932 must be sufficiently tight to prevent PEEK from escaping the mold even at the high temperatures and pressures of the manufacturing process.

The lower piece 932 includes a main recess 936 and a protrusion recess 938. The upper piece 934 includes a main recess 940 and a protrusion recess 942. When fitted together the corresponding recesses of the upper and lower pieces 934 and 932 match up. For example, the main recesses 936 and 940 match up to form a recess to shape the main body 102 of the exemplary prosthesis 100, with protrusion recesses 938 and 942 matched up to form the orientation protrusion 104.

As mentioned previously, the precise shapes, curves, tapers, tangents and cross-sections of the prosthesis 100 are configured for the specific application of the prosthesis. To that end, the main recesses 936 and 940 of the mold are shaped to form the desired shapes, curves, tapers, tangents and cross-sections. Further, the mold may include features for creating a combination of the precise surface textures, surface pockets and visual markers desired in a particular prosthesis. For example, in some embodiments the mold includes projections or recesses for creating a corresponding visual marker in the prosthesis. In some embodiments portions of the mold have a textured surface, while other portions of the mold have a smooth surface, which causes the prosthesis to have corresponding textured and smooth surfaces.

With respect to heating the PEEK 906, the PEEK is heated at a temperature range between 600° and 800° Fahrenheit. More particularly, in one embodiment, regular viscosity PEEK-OPTIMA™ (LT1) is melted at a temperature between 650° and 720° Fahrenheit. In embodiments utilizing complex geometries or large cross-sections, increasing the melting temperature to greater than 720° Fahrenheit allows the material to flow easier into the mold and fully fill the mold. Higher temperatures are also used when using various materials, such as impregnated PEEK polymers.

Once heated, the PEEK can be injected into the mold 930. The PEEK is injected at a temperature between 300° and 500° Fahrenheit. Further, the melted PEEK is injected with a pressure range between 5,000 and 15,000 psi. More particularly, in some embodiments the pressure range is between 10,000 and 13,000 psi. PEEK is inserted into the mold until the main recesses 936 and 940, and protrusion recesses 938 and 942 are completely filled. When the portions of the mold for forming the prosthesis 100 are completely filled, the PEEK will have a peak pressure between 15,000 and 25,000 psi. More particularly, in some embodiments the peak pressure is between 19,000 and 23,000 psi. Further, when filled the back pressure of the PEEK is in a range between 500 and 1,500 psi.

Once the mold 930 is filled with melted PEEK to the appropriate level, the injected PEEK is then, in step 910, held in the mold until the PEEK substantially sets. The hold pressure or packing pressure can be in a range between 5,000 and 25,000 psi. More particularly, in some embodiments the hold pressure is between 18,000 and 23,000 psi. Further, in some embodiments the hold pressure is determined by decreasing the pressure approximately 200 psi from the peak pressure.

After the PEEK is set, it can be removed from the mold 930, in 912. Once removed from the mold, the prosthesis is subjected to additional processing, in step 914. However, in some embodiments, no additional processing is performed on the prosthesis. That is, once the prosthesis is removed from the mold it is in its final, useable form.

The PEEK prosthesis removed from the mold 930 can be subjected various types of additional processing. For example, the prosthesis may be coated with one or more materials in order to obtain specific desired exterior surface characteristics. Suitable coating materials may include polycarbonates, polyethers, silicone enhanced, silicone modified, and silicone dipped polyurethanes, lubricants, and wetting agents. In other embodiments, ceramic materials such as aluminum oxide or alumina, zirconium oxide or zirconia, compact of particulate diamond, or pyrolytic carbon are suitable coating materials.

Where the prosthesis is not molded to include the appropriate openings for receiving installation tools, the openings are prepared. The openings are prepared by various methods, including drilling, machining, or other suitable methods. Once the openings are prepared, tools may be inserted into the openings to test the fit.

For example, in some embodiments markers are added to the prosthesis to provide radiological detection. Various suitable markers can be embedded or blended into the polymer compound so that the prosthesis becomes radiopaque. Additionally, visual markers can be added by vapor-honing, laser etching, or other appropriate methods.

While the molding example uses PEEK as the prosthesis, it is also contemplated that polyurethane (PU) could be used in place of PEEK. For example, some polyurethanes may have a lower durometer than PEEK. Therefore, a prosthesis 100 formed of PU may have increased flexibility. Thus, it may be more susceptible to deformation during implantation to fit between the narrow passage of the vertebral lip and/or more susceptible to deformation by an instrument (tube, channel, or walls). But it still may provide sufficient structural support to aid in height maintenance. Further, the soft segments and lubricious properties of PU may improve the articulation and wear within the vertebral space. The flexibility of the PU also may enhance the fit with an inserter instrument by press fit, snap lock, or self-threading attachment features.

The external surface may exhibit an outer lubricious surface of HA as described above or silicone enhanced/modified PU. In some embodiments, the outer shell coating process is performed in colored blends of the PU so that wear surfaces or stress states could be identified post implantation or test. The color process also may aid in identifying sizes or specific performance parameters (stiffness) of specialized devices. The color could also identify mechanically enabled collapsing devices to those exhibiting unitary construction. Further, when coated with HA as described above, insertion and distraction into tight spaces may be more easily accomplished than with some other polymer.

In some examples, the polymeric structure may be a mechanically expanding arrangement to allow compression or smaller fit through the vertebral border and then expand via an instrument to enable the device to be taller or rounder in shape to fit the natural sulcus of the endplates and thereby resist expulsion.

Other modifications of the present disclosure would be apparent to one skilled in the art. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that spatial references, such as "horizontal," "vertical," "top," "side," "upper," "lower," "bottom," "depth," "height," "raised," "left," and "right," are for illustrative purposes and can be varied within the scope of the disclosure.

We claim:

1. An intervertebral prosthetic device for implantation within a disc space between adjacent first and second vertebral endplates, comprising:
   a body including an outer surface bearing portion configured to interface with and articulate relative to the second vertebral endplate;
   the body being sized in at least one direction to fit inside a boundary defined by a travel path of the first vertebra relative to the second vertebra, the travel path forming an arc about a center of rotation of the first vertebra, the travel path being spaced from the center of rotation a distance substantially equivalent to the distance from the center of rotation to the second vertebral endplate or vice versa, the body being shaped in a manner that results in a relatively small area of contact between the second vertebral endplate and the body; and
   a prosthetic endplate including a first portion that defines a depression configured to receive the body and a protruding portion, the prosthetic endplate further including a second portion including an inner surface configured with an opening extending through upper and lower surfaces of the second portion for disposal of the protruding portion, the second portion configured to interface directly with the first vertebral endplate.

2. The prosthetic device of claim 1, wherein the body is non-symmetrical such that the body is sized to fit inside the boundary in one direction and sized such that the body does not fit within the boundary in a transverse direction.

3. The prosthetic device of claim 1, wherein the bearing surface has a first radius of curvature in the at least one direction and a second radius of curvature in a direction transverse to the at least one direction, wherein the first radius of curvature and the second radius of curvature are different.

4. The prosthetic device of claim 1, wherein the device is formed of a polymeric material.

5. The prosthetic device of claim 1, wherein the device is formed of at least one of PEEK and polyurethane.

6. The prosthetic device of claim 1, further including a coating about the body configured to provide lubricity between the outer surface and at least one of the first and second vertebral endplates.

7. The prosthetic device of claim 1, wherein the device is sized and shaped to provide impingement free articulation through a flexion/extension range equal to or greater than 15 degrees.

8. The prosthetic device of claim 1, wherein the bearing portion forms a hemispherical surface.

9. The prosthetic device of claim 1, wherein the bearing surface is cylindrical.

10. The prosthetic device of claim 1, wherein the first portion is configured to interface directly with the first vertebral endplate when the protruding portion is disposed in the opening.

11. The prosthetic device of claim 1, wherein the first portion has a maximum width that is equivalent to a maximum width of the second portion such that an exterior surface of the second portion extending transverse to the opening is aligned with an exterior surface of the first portion when the protruding portion is disposed in the opening.

12. An intervertebral prosthesis implantable within a disc space, disposed between adjacent first and second vertebral endplates, comprising:
   a spherical body formed of medical-grade polymeric material, the body being sized in at least one direction to fit inside a boundary defined by a travel path of the first vertebra relative to the second vertebra, the travel path forming an arc about a center of rotation of the first vertebra, the travel path being spaced from the center of rotation a distance substantially equivalent to the distance from the center of rotation to the second vertebral endplate or vice versa, the body being shaped in a manner that results in a relatively small area of contact between the second vertebral endplate and the body;
   the body having an outer surface comprising an upper bearing portion and a lower bearing portion, at least one of the upper and lower bearing portions being configured to articulate relative to one of the first and second vertebral endplates, the at least one of the upper and lower bearing portions including fluid-receiving pores and having a hardness that permits deformation of the main body to expel the fluid from the pores under a load applied by the respective first or second vertebral endplate; and
   a prosthetic endplate including a first portion that defines a depression configured to receive the body and a protruding portion, the prosthetic endplate further including a ring-shaped second portion including an inner surface configured with an opening extending through upper and lower surfaces of the second portion for disposal of the protruding portion, the second portion configured to interface directly with the first vertebral endplate.

13. The intervertebral prosthesis of claim 12, wherein the polymeric material has a hardness within the range of 80-90 Durometer Shore D.

14. The intervertebral prosthesis of claim 12, including a film coating on the body, the film coating being one of a lubricating agent, a wetting agent, and a bone morphogenetic protein.

15. The intervertebral prosthesis of claim 12, wherein the body has one of a generally spherical shape, a generally ellipsoidal shape, and a generally paraboloidal shape.

16. The intervertebral prosthesis of claim 12, wherein the body has a first cross-sectional generally rectangular shape and a second cross-sectional generally oval shape.

17. The intervertebral prosthesis of claim 12, wherein the surface has a relatively rough area and a relatively smooth area.

18. The intervertebral prosthesis of claim 12, further comprising a marker of a radiopaque material.

19. The intervertebral prosthesis of claim 12, further comprising:
- a first marker positioned in a first segment of the prosthesis, and a second marker positioned in a second segment of the prosthesis; and
- the first marker being remotely distinguishable from the second marker.

20. The intervertebral prosthesis of claim 12, wherein the medical-grade polymeric material is one of a polyetheretherketone (PEEK) and a polyurethane (PU).

\* \* \* \* \*